(12) United States Patent
Killick et al.

(10) Patent No.: US 6,589,913 B1
(45) Date of Patent: Jul. 8, 2003

(54) AGROCHEMICAL COMPOSITION

(75) Inventors: Robert W. Killick, Victoria (AU); Andrew R. Killick, Victoria (AU); Peter W. Jones, Victoria (AU); Peter R. Wrigley, Victoria (AU); John D. Morrison, Victoria (AU)

(73) Assignee: Victorian Chemicals International Pty Ltd., Richmond (AU)

( * ) Notice: Subject to any disclaimer, the term of this patent is extended or adjusted under 35 U.S.C. 154(b) by 0 days.

(21) Appl. No.: 09/831,303

(22) PCT Filed: May 5, 2000

(86) PCT No.: PCT/AU00/00415

§ 371 (c)(1), (2), (4) Date: May 8, 2001

(87) PCT Pub. No.: WO00/67571

PCT Pub. Date: Nov. 16, 2000

(30) Foreign Application Priority Data

May 5, 1999 (AU) ............................................. PQ 0176

(51) Int. Cl.[7] ........................ A01N 25/04; A01N 57/02
(52) U.S. Cl. ........................................ 504/206; 504/363
(58) Field of Search ............................... 504/127, 128, 504/142, 144, 145, 206, 323, 362

(56) References Cited

U.S. PATENT DOCUMENTS

| | | | |
|---|---|---|---|
| 4,853,026 A | 8/1989 | Frisch et al. ................... | 71/86 |
| 5,411,932 A | 5/1995 | Yoshida et al. ............. | 504/132 |
| 6,117,816 A | * 9/2000 | Jimoh et al. ................ | 504/118 |
| 6,133,199 A | 10/2000 | Soula et al. | |
| 2001/0019996 A1 | 9/2001 | Soula et al. | |

FOREIGN PATENT DOCUMENTS

| | | |
|---|---|---|
| AU | 80459/94 | 6/1995 |
| AU | 733912 B2 | 12/1998 |
| EP | 0 508 022 | * 10/1992 |
| EP | 0 598 515 | 5/1994 |
| WO | WO 93/00809 | 1/1993 |
| WO | WO 98/09518 | 3/1998 |
| WO | WO 98/17110 | 4/1998 |
| WO | WO 98/53680 A1 | 12/1998 |
| WO | WO 99/00012 A2 | 1/1999 |
| WO | WO 99/05914 A1 | 2/1999 |
| WO | WO 00/32045 A1 | 6/2000 |

OTHER PUBLICATIONS

Ross et al. Applied Weed Science. Minneapolis, MN: Burgess Pub. Co. 1985. p. 108.*

Tabbush et al., "Chemicals for the Forester: What About Additives?" Forestry and British Timber, Feb. 1988, pp. 12–13.

Turner, "Additives for Use with Herbicides, a Review," Malaysian Plan Protection Society, J. Pl. Prot. Troples 1(2):: pp. 77–86, No date.

Turner et al., "Studies with Solubilized Herbicide Formulations," Proceedings 12th British Weed Control Conference, 1974, pp. 177–184.

Turner, Symposium on Application and Biology, "Studies with Alternative Glyphosate Formulations," 1985, pp. 135–145.

Turner, "Preliminary Results of Research into Improving Herbicide Performance by the Use of Additives," 1975, pp. 82–90.

* cited by examiner

*Primary Examiner*—S. Mark Clardy
(74) *Attorney, Agent, or Firm*—Foley & Lardner

(57) ABSTRACT

An agrochemical composition with enhanced activity and phase stability is provided comprising:

a) glyphosate present in an amount which is not in excess of about 25% b) one or more lipophilic solvents present in an amount which is not in excess of about 80% c) one or more lipophobic plant nutrients present in an amount which is not in excess of about 50% d) one or more oil soluble bases present in an amount which is not in excess of about 50% wherein the oil soluble base forms a lipophilic solvent soluble complex with glyphosate which is capable of coupling or assisting coupling of the lipophobic plant nutrients with the lipophilic solvents.

28 Claims, No Drawings

AGROCHEMICAL COMPOSITION

This application has been filed under 35 USC 371 as the national stage of international application PCT/AU00/00415, filed May 5, 2000.

FIELD OF THE INVENTION

The invention relates to an agrochemical composition. More particularly, this invention relates to a composition which includes both a biologically active ingredient and adjuvants.

BACKGROUND OF THE INVENTION

In this specification, where a document, act or item of knowledge is referred to or discussed, this reference or discussion is not to be taken as an admission that the document, act or item of knowledge or any combination thereof was at the priority date:

(a) part of common general knowledge; or (b) known to be relevant to an attempt to solve any problem with which this specification is concerned.

Farmers use many agrochemicals to protect or improve their crops. Often, farmers will add adjuvants to a prepared solution containing biologically active ingredients (hereinafter referred to as "actives") and water to enhance their performance. Sometimes the adjuvants must be added to ensure optimum performance of the actives in a variety of conditions which may otherwise inhibit it, for example, hard water, high temperatures, poor growing conditions.

Whilst the following discussion highlights the invention with relation to herbicides, it is believed that the same principles apply to other actives such as plant hormones, insecticides, crop desiccants or crop defoliants.

Glyphosate is a non-selective herbicide. It is commonly used in domestic, industrial and agricultural situations to control weeds. In the agricultural industry, its use may be limited by the fact that glyphosate will kill most plants including the desired crop depending on the application rate and/or resistance level. Non-selective herbicides can also be used to control weeds in cropping situations where the crop has either been bred or genetically modified to be resistant to the herbicide.

However, when a field is fallow there is no crop for the farmer to be concerned about and glyphosate is often used to prevent weeds from maturing to produce a multitude of seeds which will germinate and cause problems when a crop is later grown on that field.

There is a growing trend to combine herbicides with adjuvants which increase the efficacy of the herbicide. There are two trends in this area. On the one hand, adjuvants are developed as separate compositions which are added to the herbicide at the time of use. On the other hand, formulations have been developed which contain both the herbicide and the adjuvant.

The types of substances which are used as adjuvants include ammonium salts and other plant nutrients, wetting agents, spray drift retardants and lipophilic solvents. Ammonium salts are believed to minimize the deleterious effects of hard water on herbicidal performance and to provide nutrition to the plant which enhances herbicidal performance. Wetting agents improve the leaf coverage of the herbicide. Lipophilic solvents keep the herbicide in liquid form as the herbicide will be ineffective if it dries on the foliage and can also assist the penetration of the herbicide into the plant.

The farmer may combine all these additives with the herbicide when the tank mix is prepared but the farmer may not know whether these components are compatible with each other. Some additives or adjuvants can actually antagonise each other and decrease the activity of the agrochemical. It is also inconvenient since there are several components which must be bought, measured and combined.

Farmers are always looking for more efficacious and convenient ways to enhance the performance of active ingredients. They would also prefer to simply apply a single composition which they know will have optimum performance.

A composition which contains actives when formulated with both plant nutrients and lipophilic solvents may have benefits over other formulations of the same actives or tank mixes of the individual components. However, this has not been possible to evaluate because preparing a homogeneous blend of these components is not easily achieved as they are not readily coupled together.

For example, it is known that formulations of glyphosate and ammonium sulfate can be readily produced because both of these substances are water soluble. However, the polar nature of glyphosate and ammonium sulfate has prevented the formulation of useful compositions which include lipophilic solvents since glyphosate and ammonium sulfate are essentially insoluble in lipophilic solvents.

SUMMARY OF THE INVENTION

It has surprisingly been found that a composition which includes one or more oil soluble bases will enable a homogeneous blend to be formed of actives which include organic acids, plant nutrients (e.g. ammonium salts), water and lipophilic solvents.

According to one aspect of the invention, a homogeneous liquid agrochemical composition is provided which comprises:

(a) not in excess of about 25% of one or more organic acids used as an active;

(b) not in excess of about 80% of one or more lipophilic solvents;

(c) not in excess of about 50% of one or more plant nutrients (such as ammonium salts of inorganic anions); and (d) not in excess of about 50% of one or more oil soluble bases wherein the oil soluble base forms a lipophilic solvent soluble complex with the organic acid;

wherein all proportions are calculated weight/weight on a dry basis based on the total composition.

Preferably, the agrochemical composition comprises:

(a) from 2 to 12% of one or more organic acids used as an active;

(b) from 10 to 50% of one or more lipophilic solvents;

(c) from 2 to 20% of one or more plant nutrients (such as ammonium salts of inorganic anions); and (d) from 2 to 20% of one or more oil soluble bases.

The organic acids may be selected from the group including glyphosate, gibberellic acid, 2,4-D, dinitrocresol, acifluorfen, benazolin, bilanafos, blasticidin-S, chloramben, chlorflurenol, chlorimuron, chloroacetic acid, chlorthal, clodinafop, cloprop, clopyralid, cloquintocet, cloxyfonac, 4-CPA, flamprop, flamprop-M, fluazifop, fluazifop-P, fluoroglycofen, flupropanate, flurenol, fluroxypyr, fosamine, fosetyl, glufosinate, halosulphuron, haloxyfop, imazapyr, imazaquin, imazethapyr, indol-3-ylacetic acid, 4-indol-3-ylbutyric acid, kasugamycin, quinclorac, quinmerac, quizalofop, quizalofop-P, sulfometuron, 2,3,6-TBA, tecloftalam, thifensulfuron, triclopyr and triflusulfuron. Preferably the organic acid is glyphosate.

The lipophilic solvents may be petroleum fractions, vegetable oils, alkyl esters of fatty acids, fatty alcohols, guerbet alcohols or any combination thereof. The vegetable oils include medium chain triglycerides.

The plant nutrients include ammonium salt of inorganic anions (such as ammonium sulfate and ammonium phosphates) which are known to minimize the deleterious effects of hard water on the performance of actives. Preferably, the ammonium salt is ammonium sulfate. If an anhydrous ammonium salt is used then water may need to be added to the composition. However, if the ammonium salt is already in solution then additional water will probably not be necessary.

The oil soluble bases which may be used include fatty amines, fatty quaternary ammonium hydroxides, fatty betaines and calcium overbasedphenates which will couple with the active acid to form an oil soluble complex. Preferably, N,N-dialkyl fatty amines are used. For example, N,N dimethyllaurylamine or dimethylcocoamine.

According to another preferred embodiment of the invention, the agrochemical composition optionally contains other components to improve the form of the composition. These other components may be added to form a microemulsion. Typically, emulsifiers may be used and selected from emulsifiers which may be nonionic, anionic, cationic or amphoteric. Other components which may be added include co-solvents, coupling agents or diluents used to form a micro-emulsion. Preferably, the other components used to form a micro-emulsion with alkyl esters of fatty acids as the lipophilic solvent are a combination of nonionic emulsifiers, cationic emulsifiers and co-solvents. More preferably, with ethyl esters of fatty acids the other components are alkyl polysaccharides, propylene glycol, fatty alkanolamides and cetyl trimethyl anunonium chloride.

Preferably, the nonionic emulsifiers are alkyl polysaccharides, sorbates, polysorbates, alcohol ethoxylates, alkylphenol ethoxylates, glycols or fatty alkanolamides. Alkyl polysaccharides are sometimes called alkyl polyglucosides, alkyl glucosides or alkyl saccharides. An example of a fatty alkanolamide is oleyldiethanolamide. The glycols include propylene glycol, 1,3-butylene glycol, hexylene glycol, and polypropylene glycols.

The cationic emulsifiers are well known to those skilled in the art, and it is recognised there are a multitude of combinations. Preferably, the cationic emulsifiers are quaternary cationic emulsifiers, for example, alkyltrimethylammonium chloride, alkyl dimethylbenzylammonium chloride, alkylpyridium chloride, or alkylimidazolium chloride. More preferably, the cationic emulsifiers are fatty quaternary ammonium chlorides.

According to another preferred embodiment, the agrochemical composition further comprises one or more other available adjuvant components. The adjuvant component may be selected from nonionic emulsifiers, cationic emulsifiers, pH modifiers, spray drift retardants and wetters.

According to a second form of the invention, there is provided a method for enhancing the activity of an organic acid used as an active in an agrochemical composition comprising the step of incorporating the organic acid in a homogeneous liquid agrochemical composition comprising:

(a) not in excess of about 25% of one or more organic acids used as an active;

(b) not in excess of about 80% of one or more lipophilic solvents;

(c) not in excess of about 50% of one or more plant nutrients (such as ammonium salts of inorganic anions); and (d) not in excess of about 50% of one or more oil soluble bases wherein the oil soluble base forms a lipophilic solvent soluble complex with the organic acid;

wherein all proportions are calculated weight/weight on a dry basis based on the total composition.

According to a third form of the invention, there is provided a method of treating vegetation comprising the step of applying a homogeneous liquid agrochemical composition comprising:

(a) not in excess of about 25% of one or more organic acids used as an active;

(b) not in excess of about 80% of one or more lipophilic solvents;

(c) not in excess of about 50% of one or more plant nutrients (such as ammonium salts of inorganic anions); and (d) not in excess of about 50% of one or more oil soluble bases wherein the oil soluble base forms a lipophilic solvent soluble complex with the organic acid;

wherein all proportions are calculated weight/weight on a dry basis based on the total composition.

EXAMPLES

The invention will now be further explained and illustrated by reference to the following non-limiting examples.

| Lipophilic solvents, plant nutrients, organic acids and oil soluble bases used | |
|---|---|
| 1,3 Butanediol | ex Hoechst Celanese, U.S.A. |
| 2,4-D | (2,4-dichlorophenoxy) acetic acid from UNISUN International, Australia |
| '880' ammonia | ex Orica, Australia |
| Ammonium sulphate | >99% purity ex Redox Chemicals, Australia. |
| Algene SC25 | 25% paste of stearyldimethylbenzyl ammonium chloride ex ICI Ltd, UK |
| Alkadet 15 | 70% solution of alkyl polysaccharide ex Huntsman Corporation, Australia |
| Citric acid | ex Citric Belge, Belgium |
| Empigen BB/AU | 28% solution of cocobetaine ex Albright and Wilson, Australia |
| Esterol 112 | methyl esters of canola oil fatty acids ex Victorian Chemical Company, Australia |
| Esterol 123 | approximately 80% w/w ethyl and 20% w/w methyl esters of Canola Oil fatty acids ex Victorian Chemical Company, Australia |
| Farmin DMC | dimethylcocoamine ex KAO, Philippines |
| Glufosinate | 4-[hydroxy(methyl)phosphinoyl]-DL-homoalanine ammonium salt as 50% aqueous solution ex Aventis, Germany. |
| Glyphosate | N-(phosphonomethyl)glycine (98% min) ex Davison Industries, Australia. |
| Glyphosate CT | 450 g/L glyphosate ex Nufarm, Australia |
| Isopropanol | ex Redox Chemicals, Australia |
| Noram O | oleylamine ex Elf Atochem, Australia |
| Oxamin LO | 30% solution of lauryldimethylamine oxide ex Huntsman Corporation, Australia |
| Propylene Glycol | ex Consolidated Chemical Company, Australia |
| Quatramine C16/29 | 29% solution of cetyl trimethyl ammonium chloride ex APS, Australia |
| Quatramine NC50 | 50% solution of alkyldimethylbenzene ammonium chloride 50% solution ex APS, Australia |
| Radiamine 6765 | dimethyl laurylamine ex Fina Chemicals Belgium. |
| Radiaquat 6465 | 30% solution of lauryl trimethyl ammonium chloride ex Fina Chemicals, Belgium. |
| Shell P830 | 70 sec neutral paraffinic oil ex Shell, Australia |
| Sulphuric acid | 98% commercial grade ex Orica, Australia |
| Sylgard 309 | Silicone based wetting agent ex Dow Corning, Australia |
| Teric 16M2 | fatty amine ethoxylate ex Huntsman Corporation, Australia. |

-continued

| Lipophilic solvents, plant nutrients, organic acids and oil soluble bases used | |
|---|---|
| Teric GN9 | nonylphenol 9 moles ethylene oxide ex Huntsman Corporation, Australia |
| Terwet 3001 | 70% solution of alkyl polysaccharide ex Huntsman Corporation, Australia |
| Vicamid 182 | oleylimidazoline ex Victorian Chemical Company, Australia |
| Vicamid 825 | oleyldiethanolamide ex Victorian Chemical Company, Australia |
| Urea | ex Orica, Australia |

The following compositions incorporating glyphosate, glufosinate, 2,4-D or mixtures thereof were prepared, some of which have been evaluated for herbicidal activity in the Examples. Compositions 1 to 9 have also been established to be stable homogeneous blends, that is, the composition remained clear without phase separation for at least 48 hours through the temperature range from 0 to 40° C. Compositions 10 to 16 have only been evaluated at ambient and appear as either a semi-stable emulsion or a more stable micro-emulsion.

| Other component-coupling agents | | | | | |
|---|---|---|---|---|---|
| Sulphuric acid | — | — | — | — | — |
| Propylene glycol | 3 | 5.3 | 4.3 | 6.2 | — |
| Isopropanol | — | — | — | — | 3.0 |
| Citric acid | — | — | — | — | — |
| '880' Ammonia | — | — | 0.9 | — | — |
| 1,3-butanediol | — | — | 4.3 | 6.2 | 3.0 |
| Other component-nonionic surfactant | | | | | |
| Vicamid 825 | 10 | 5.3 | 8.7 | 21.6 | 9.3 |
| Vicamid 182 | — | — | — | — | — |
| Sylgard 309 | — | — | — | — | — |
| Terwet 3001 | — | — | — | — | 3.5 |
| Teric GN9 | — | — | — | 3.1 | — |
| Alkadet 15 | 5 | 3.2 | 4.3 | 2.5 | — |
| Other component-cationic surfactant | | | | | |
| Radiaquat 6465 | 5 | — | — | — | — |
| Quatramine NC50 | — | — | — | 6.2 | — |
| Quatramine C16/29 | — | 5.3 | 13.9 | — | 6.5 |
| Oxamin LO | — | — | — | — | — |
| Algene SC25 | — | — | — | — | — |
| Oil soluble base | | | | | |
| Teric 16M2 | — | 10.5 | — | 9.3 | — |
| Radiamine 6765 | 10 | — | — | — | — |
| Noram O | — | — | — | — | 2.0 |
| Farmin DMC | — | — | — | — | 11.0 |
| Empigen BB/AU | — | — | 8.7 | — | — |
| Lipophilic solvent | | | | | |
| Shell P830 | — | — | — | 18.5 | — |
| Esterol 123 | 30 | 31.6 | 26.1 | — | 25.0 |
| Esterol 112 | — | — | — | — | — |
| Plant nutrient | | | | | |
| Water | 21 | 23.2 | 17.4 | 16.7 | 21.0 |
| Urea | — | — | — | — | 1.0 |
| Ammonium sulfate | 10 | 10.5 | 8.7 | 6.2 | 7.0 |
| Organic acid | | | | | |
| Glyphosate | 6 | 5.3 | 2.6 | 3.7 | 7.7 |
| Glufosinate | — | — | — | — | — |
| 2,4-D | — | — | — | — | — |
| Composition | 1 | 2 | 3 | 4 | 5 |

-continued

| Other component-coupling agents | | | | | |
|---|---|---|---|---|---|
| Sulphuric acid | — | — | 2.0 | — | — | — |
| Propylene glycol | — | — | — | 5.5 | — | — |
| Isopropanol | 3.0 | 3.2 | — | — | — | — |
| Citric acid | — | — | — | 0.4 | — | — |
| '880' Ammonia | — | — | — | — | — | — |
| 1,3-butanediol | 3.0 | 3.2 | 5.0 | — | — | — |
| Other component-nonionic surfactant | | | | | | |
| Vicamid 825 | 9.3 | 8.0 | 8.0 | — | — | — |
| Vicamid 182 | — | — | — | — | — | — |
| Sylgard 309 | — | — | — | — | — | — |
| Terwet 3001 | 3.5 | — | 5.5 | — | — | — |
| Teric GN9 | — | — | — | — | — | — |
| Alkadet 15 | — | — | — | 5.5 | — | — |
| Other component-cationic surfactant | | | | | | |
| Radiaquat 6465 | — | — | — | — | — | — |
| Quatramine NC50 | — | — | — | — | — | 10 |
| Quatramine C16/29 | 3.6 | 7.0 | 5.0 | 5.5 | 10 | — |
| Oxamin LO | — | — | — | — | — | — |
| Algene SC25 | 4.6 | — | — | — | — | — |
| Oil soluble base | | | | | | |
| Teric 16M2 | — | — | — | — | — | — |
| Radiamine 6765 | — | — | — | — | — | — |
| Noram O | 2.0 | 2.1 | 2.5 | 2.2 | — | 3 |
| Farmin DMC | 11.0 | 11.8 | 7.0 | 7.7 | 10 | 7 |
| Empigen BB/AU | — | — | — | — | — | — |
| Lipophilic solvent | | | | | | |
| Shell P830 | — | — | — | — | — | 40 |
| Esterol 123 | 25.0 | — | 25.0 | 32.8 | 40 | — |
| Esterol 112 | — | 26.7 | — | — | — | — |
| Plant nutrient | | | | | | |
| Water | 19.3 | 22.5 | 18.0 | 23.0 | 20 | 30 |
| Urea | 1.0 | — | — | — | — | — |
| Ammonium sulfate | 7.0 | 7.5 | 7.0 | 11.0 | 4 | 4 |
| Organic acid | | | | | | |
| Glyphosate | 7.7 | 8.0 | — | — | 6 | 6 |
| Glufosinate | — | — | 15 | — | — | — |
| 2,4-D | — | — | — | 6.6 | — | — |
| Composition | 6 | 7 | 8 | 9 | 10 | 11 |

| Other component-coupling agents | | | | | |
|---|---|---|---|---|---|
| Sulphuric acid | — | — | — | — | — |
| Propylene glycol | 8 | — | — | — | — |
| Isopropanol | — | 3 | 3 | 3 | 3 |
| Citric acid | 1 | — | — | — | — |
| '880' Ammonia | — | — | — | — | — |
| 1,3-butanediol | — | 4 | 4 | 3 | 3 |
| Other component-nonionic surfactant | | | | | |
| Vicamid 825 | — | — | 0.5 | 9.3 | 9.3 |
| Vicamid 182 | — | — | 3 | — | — |
| Sylgard 309 | 2 | — | — | — | — |
| Terwet 3001 | 6 | 5 | 5 | 3.5 | 3.5 |
| Teric GN9 | — | — | — | — | — |
| Alkadet 15 | — | — | — | — | — |
| Other component-cationic surfactant | | | | | |
| Radiaquat 6465 | — | — | — | — | — |
| Quatramine NC50 | — | — | — | — | — |
| Quatramine C16/29 | 5 | 5 | 5 | — | — |
| Oxamin LO | — | — | — | — | 6.5 |
| Algene SC25 | — | — | — | — | — |
| Oil soluble base | | | | | |
| Teric 16M2 | — | — | — | — | — |
| Radiamine 6765 | — | — | — | — | — |
| Noram O | 3 | 3 | — | 2 | 2 |

-continued

| | | | | | |
|---|---|---|---|---|---|
| Farmin DMC | 10 | 12 | 12 | 11 | 11 |
| Empigen BB/AU | — | — | — | — | — |
| Lipophilic solvent | | | | | |
| Shell P830 | — | — | — | — | — |
| Esterol 123 | 24 | 24 | 24.5 | 25 | 25 |
| Esterol 112 | — | — | — | — | — |
| Plant nutrient | | | | | |
| Water | 22 | 22 | 23 | 21 | 21 |
| Urea | — | — | — | 1 | 1 |
| Ammonium sulfate | 10 | 10 | 8 | 7 | 7 |
| Organic acid | | | | | |
| Glyphosate | — | 6 | 6 | 7.7 | 7.7 |
| Glufosinate | — | — | — | — | — |
| 2,4-D | 10 | 6 | 6 | — | — |
| Composition | 12 | 13 | 14 | 15 | 16 |

Efficacy of Glyphosate and 2,4-D Formulations

A series of screening trials were undertaken to determine the efficacy of the compositions. All studies were carried out using commercial products (herbicides and tank added adjuvants) at recommended or reduced use rates to be able to differentiate the performance of the products. The conditions were controlled to simulate certain field conditions and are described in detail for each experiment.

Examples 1 to 4 each use the following definitions

| | |
|---|---|
| Standard conditions | After spraying, the plants were transferred to the greenhouse |
| Hot conditions | Plants in this treatment were transferred to a 30° C. constant environment room 1 hour prior to spraying application and returned immediately after spraying for 2 hours. They were then transferred to the greenhouse. |
| Rain | Rainfall was applied to plants 2 h after spray application. 10 mm of rain was applied at an intensity of 46 mm/h |
| Herbicide application | Herbicides plus additives were applied using an enclosed laboratory track-sprayer fitted with three 110° flat fan nozzles (Spray Systems Tee Jet 11001) spaced at 50 cm intervals across the boom. The boomspray moved along a fixed track at 6 km/h, sprayed at a water volume of 64 1/ha with a pressure of 200 kPa |
| Plant propagation and seedling treatment prior to spray application | Ryegrass and wild radish (5 seeds/pot) were sown at 5 mm depth in 10 cm diameter plastic pots filled with Debco potting mix (AS3743) which had been amended with macro and micro nutrients to ensure optimal growth. One week after emergence, seedlings were thinned to one uniform plant per pot. Plants were grown in a temperature-controlled greenhouse and transferred outdoors for 3 days prior to spray application in order to harden the seedling and more closely simulate field conditions |
| fresh wt # | is the weight (g/plant) # days after application. Typically a lower number indicates that the herbicide is detrimentally affecting the life of the plant to a greater degree than those treatments with higher numbers |
| visual # | visual assessment # days after application |

Plants were sprayed at 3–6 leaf stage
All treatments used 7 or 8 replicates.
Visual assessments use the following rating system
1 No damage evident
2 Probable damage
3 Obvious damage
4 Most plants affected, some sever stunting
5 All plants affected, some likely to die
6 All plants severely affected, some very likely to die
7 All plants severely affected, some dead, most others likely to die
8 Most plants dead, all others likely to die
9 All plants dead

| Materials used in comparative examples | |
|---|---|
| Amicide 500 | commercial herbicide containing 500 g/l 2,4-D ex Nufarm, Australia |
| BS1000 | commercial adjuvant containing alcohol ethoxylate wetter ex Crop Care, Australia |
| Hasten | commercial adjuvant containing 740 g/l ethyl and methyl esters of canola oil ex Victorian Chemical Company, Australia |
| Liase | commercial adjuvant containing 417 g/l ammonium sulphate ex Nufarm, Australia |
| LI700 | commercial adjuvant comprising 355 g/l soyal phospholipids and 345 g/l propionic acid ex Nufarm, Australia |
| Roundup CT Xtra | commercial herbicide composition containing 490 g/L glyphosate ex Monsanto, Australia |

Example 1

This example was undertaken to assess the efficacy of the herbicidal compositions containing glyphosate when applied to ryegrass when temperature conditions were varied. Compositions 2, 3 and 4 were used at such a rate to provide equivalent amount of glyphosate as the commercial product Roundup CT Xtra. Each of the compositions was applied at one eighth and one quarter of the standard recommended rates in both Standard and Hot conditions.

Test results with ryegrass shoots

| Product | rate (ml/l) | visual 19 | visual 28 | fresh wt 33 |
|---|---|---|---|---|
| Standard conditions | | | | |
| Roundup CT Xtra | 1.8 | 2 | 3 | 3.80 |
| Roundup CT Xtra | 3.6 | 4 | 5 | 1.04 |
| Composition 2 | 16 | 4 | 5 | 1.31 |
| Composition 2 | 33 | 8 | 8 | 0.18 |
| Composition 3 | 33 | 5 | 6 | 0.54 |
| Composition 3 | 67 | 7 | 7 | 0.18 |
| Hot conditions | | | | |
| Roundup CT Xtra | 1.8 | 3 | 3 | 3.00 |
| Roundup CT Xtra | 3.6 | 6 | 6.5 | 0.63 |
| Composition 2 | 16 | 6 | 6 | 1.23 |
| Composition 2 | 33 | 9 | 9 | 0.10 |
| Composition 4 | 23 | 5 | 5 | 1.61 |
| Composition 4 | 46 | 8 | 7 | 0.10 |

Compositions 2, 3 and 4 all outperformed the commercial standard Roundup CT Xtra under standard or hot conditions and at either the lower or higher rates using either the visual or fresh weight assessment method. These results clearly illustrate that each of Compositions 2 to 4 are more effective than the commercial product.

Example 2

This example was undertaken to assess the efficacy of the herbicidal compositions containing glyphosate when applied to ryegrass when water hardness is varied. Commercial Glyphosate products were used either alone or with tank added adjuvants. Application rates were designed to provide equivalent amount of glyphosate within each experiment which was equivalent to 120g ai/ha or about one quarter normal use rate.

Water hardness is measured in World Health Organisation units of hardness (WHO). One WHO is equivalent to 343 ppm of $CaCO_3$. Tap refers to Melbourne tap water hardness (approximately 20 ppm).

All results are reported as fresh weight (g/plant)19 days after application. The Unsprayed Control had a fresh weight of 1.726.

| Test results with ryegrass shoots | | | | | | |
|---|---|---|---|---|---|---|
| Glyphosate product | Rate (ml/l) | Tank additive/rate | tap | 1 WHO | 3 WHO | Hot |
| Glyphosate CT | 4.2 | LI700 0.25% | 0.401 | 0.487 | 1.183 | 0.647 |
| Glyphosate CT | 4.2 | BS1000 0.1% Liase 2.0% | 0.127 | 0.130 | 0.158 | 0.266 |
| Glyphosate CT | 4.2 | Hasten 0.25% | 0.186 | 0.325 | 1.588 | 0.223 |
| Roundup CT Xtra | 3.8 | — | 0.264 | 0.534 | 1.684 | 0.293 |
| Composition 5 | 24 | — | 0.176 | 0.149 | 0.555 | 0.148 |
| Composition 6 | 24 | — | 0.141 | 0.138 | 0.559 | 0.124 |

Hard water is known to have a detrimental effect on the efficacy of organic acids such as glyphosate. Sulphates and other inorganic anions can be used to counter the loss of activity associated with hard water. Hot conditions increase the evaporation rate of the spray water and thereby can leave the glyphosate dry on the foliage rendering it less available for absorption into the plant.

Example 2 clearly shows this effect where the use of Liase and BS1000 with glyphosate prevents greatly reduced efficacy as the water hardness increases. Compositions 5 and 6 also provide some protection against water hardness although the efficacy at 3 WHO is significantly reduced when compared with that in either 1 WHO or tap water.

Under Hot conditions, Compositions 5 and 6 are the most efficacious compositions in this study. Further, Compositions 5 and 6 are the only compositions for which the results are better for Hot than Standard.

It should be noted that in this study, Liase at 2.0% provides the full recommended use rate of ammonium sulphate whilst Compositions 5 and 6 are both used at significantly lower than recommended rates (in order to maintain equivalent ai for this study). Increasing the rate of Compositions 5 and 6 will also provide additional ammonium sulphate which should counter the high levels of water hardness.

In conclusion, Compositions 5 and 6 both provide increased efficacy when compared with the glyphosate product used alone. They also outperform glyphosate when used with commercial adjuvants under most of the conditions evaluated. It should be noted that sufficient ammonium sulphate is required to counter hard water effects.

Example 3

This example was undertaken to assess the efficacy of the herbicidal compositions containing glyphosate when applied at 120 g ai/ha to wild radish under Standard, rain and hard water/hot/rain conditions.

All results are reported as fresh weight (g/plant)17 days after application. The Unsprayed Control had a fresh weight of 33.2.

| Test results with wild radish | | | | | |
|---|---|---|---|---|---|
| Glyphosate product | Rate (ml/l) | Tank additive/rate | tap | tap/ rain | 1 WHO/ hot/rain |
| Glyphosate CT | 6.9 | LI700 0.25% | 13.0 | 24.2 | 28.6 |
| Glyphosate CT | 6.9 | BS1000 0.1% Liase 2.0% | 13.3 | 32.5 | 33.0 |
| Roundup CT Xtra | 6.4 | — | 12.8 | 35.3 | 29.6 |
| Composition 5 | 41 | — | 8.6 | 28.9 | 23.0 |
| Composition 6 | 41 | — | 11.1 | 25.5 | 20.7 |

Compositions 5 and 6 provided similar or slightly better performance than the other materials tested under Standard conditions. Both studies where rain was applied reduced the efficacy of all compositions. Compositions 5 and 6 were more effective in hard water/hot/rain than the other compositions and outperformed all but the Glyphosate CT/LI700 composition under tap/rain.

Composition 6 contained stearyldimethyl(benzyl) ammonium chloride as part of the cationic surfactant component which was speculated may provide some rainfastness.

Composition 6 when compared with Composition 5 showed measurable improvement when rain was applied.

Example 4

This example was undertaken to assess the efficacy of herbicidal compositions containing 2,4-D when applied to wild radish. All results are reported as fresh weight (g/plant) 24 days after application with visual assessment 21 days after spraying reported in brackets under the fresh weight. The Unsprayed Control had a fresh weight of 18.77.

| 2,4-D product | rate (ml/l) | Tank additive/rate | tap | 1 WHO | 2 WHO | 4 WHO |
|---|---|---|---|---|---|---|
| Amicide 500 | 6.6 | — | 16.45 (6) | 17.89 (5.5) | 17.79 (4) | 18.59 (4.5) |
| Amicide 500 | 6.6 | Liase 0.2% | 11.37 (6.5) | 15.83 (5.5) | 16.34 (5) | 3.71 (6) |
| Amicide 500 | 6.6 | Liase 2.0% | 17.44 (6.5) | 17.24 (5.5) | 17.14 (6) | 17.81 (6) |
| Composition 9 | 50 | — | 19.70 (6) | 15.40 (5) | 10.75 (5.5) | 11.16 (7) |

The application of 2,4-D causes an exaggerated auxin (plant hormone) response in sensitive plants. In wild radish, characteristic damage includes thickening of the leaf petiole and epinasty of stems and leaves. In some situations fresh weight reduction is not a reliable response because damaged plants may have some stem and petioles that are thicker and heavier than normal. Minor effects may not be well correlated with fresh weight. A visual assessment has been included to assist with interpretation.

From the results, Composition 9 was found to have similar or improved efficacy over Amicide 500 when used either alone or in combination with Liase. Significant improvements for Composition 9 were observed as water hardness increased.

The word 'comprising' and forms of the word 'comprising' as used in this description and the claims does not limit the invention claimed to exclude any variants or additions.

Modifications and improvements to the invention will be readily apparent to those skilled in the art. Such modifications and improvements are intended to be within the scope of this invention.

What is claimed is:

1. A method for enhancing the activity of glyphosate comprising the step of incorporating no more than about 25% of glyphosate in a homogeneous liquid agrochemical composition having a phase stability of at least 48 hours comprising:
   (a) one or more lipophilic solvents present in an amount which is not in excess of about 80%;
   (b) one or more plant nutrients present in an amount which is not in excess of about 50%; and
   (c) one or more oil soluble bases present in an amount which is not in excess of about 50% wherein the oil soluble base forms a lipophilic solvent soluble complex with glyphosate which is capable of coupling or assisting coupling of the plant nutrients with the lipophilic solvents;
   wherein all proportions are calculated weight/weight on a dry basis based on the total composition.

2. A homogeneous liquid agrochemical composition having a phase stability of at least 48 hours comprising:
   (a) glyphosate present in an amount which is not in excess of about 25%;
   (b) one or more lipophilic solvents present in an amount which is not in excess of about 80%;
   (c) one or more lipophobic plant nutrients present in an amount which is not in excess of about 50%; and
   (d) one or more oil soluble bases present in an amount which is not in excess of about 50% wherein the oil soluble base forms a lipophilic solvent soluble complex with glyphosate which is capable of coupling or assisting coupling of the lipophobic plant nutrients with the lipophilic solvents;
   wherein all proportions are calculated weight/weight on a dry basis based on the total composition.

3. An agrochemical composition according to claim 2 comprising:
   (a) from 2 to 12% of glyphosate;
   (b) from 10 to 50% of one or more lipophilic solvents;
   (c) from 2 to 20% of one or more lipophobic plant nutrients; and
   (d) from 2 to 20% of one or more oil soluble bases.

4. An agrochemical composition according to claim 2 wherein the lipophilic solvents are selected from the group consisting of petroleum fractions, vegetable oils, alkyl esters of fatty acids, fatty alcohols, guerbet alcohols or any combination thereof.

5. An agrochemical composition according to claim 4 wherein the lipophilic solvents are alkyl esters of fatty acids.

6. An agrochemical composition according to claim 5 wherein the alkyl esters of fatty acids are ethyl esters of fatty acids.

7. An agrochemical composition according to claim 5 further comprising one or more other components selected from the group consisting of nonionic emulsifiers, cationic emulsifiers, co-solvents and mixtures thereof.

8. An agrochemical composition according to claim 5 further comprising one or more other components selected from the group consisting of alkyl polysaccharides, propylene glycol, fatty alkanolamides, cetyltrimethylammonium chloride and mixtures thereof.

9. An agrochemical composition according to claim 2 wherein the lipophobic plant nutrients are ammonium salts of inorganic anions.

10. An agrochemical composition according to claim 9 wherein the lipophobic plant nutrient is selected from ammonium sulfate, ammonium phosphate or mixtures thereof.

11. An agrochemical composition according to claim 2 wherein the oil soluble bases are selected from the group consisting of fatty amines, fatty quaternary ammonium hydroxides, fatty betaines, calcium overbasedphenates and mixtures thereof.

12. An agrochemical composition according to claim 11 wherein the oil soluble bases are N,N-dialkyl fatty amines.

13. An agrochemical composition according to claim 12 wherein the oil soluble bases are selected from N,N-dimethyllaurylamine, dimethylcocoamine, oleylamine or mixtures thereof.

14. An agrochemical composition according to claim 2 further comprising one or more other components to improve the form of the composition.

15. An agrochemical composition according to claim 14 wherein the other components are added to form a micro-emulsion.

16. An agrochemical composition according to claim 15 wherein the other components are selected from the group consisting of emulsifiers, co-solvents, coupling agents, diluents used to form a micro-emulsion or mixtures thereof.

17. An agrochemical composition according to claim 14 wherein the other components are emulsifiers.

18. An agrochemical composition according to claim 17 wherein the emulsifiers are selected from the group consisting of emulsifiers which are nonionic, cationic, anionic, amphoteric or mixtures thereof.

19. An agrochemical composition according to claim 18 wherein the emulsifiers are nonionic emulsifiers which are selected from the group consisting of alkyl polysaccharides, sorbates, polysorbates, alcohol ethoxylates, alkylphenol ethoxylates, glycols, fatty alkanolamides or mixtures thereof.

20. An agrochemical composition according to claim 19 wherein the cationic emulsifiers are quaternary cationic emulsifiers.

21. An agrochemical composition according to claim 20 wherein the quaternary cationic emulsifiers are fatty quaternary ammonium chlorides.

22. An agrochemical composition according to claim 2 further comprising one or more other available adjuvant components.

23. An agrochemical composition according to claim 22 wherein the other available adjuvant components are selected from the group consisting of nonionic emulsifiers, cationic emulsifiers, pH modifiers, spray drift retardants, wetters and mixtures thereof.

24. A homogeneous liquid agrochemical composition having a phase stability of at least 48 hours comprising
   (a) from 2 to 12% of glyphosate;
   (b) from 10 to 50% of one or more alkyl esters of fatty acids;
   (c) from 2 to 20% of one or more ammonium salts of inorganic anions; and
   (d) from 2 to 20% of one or more N,N-dialkyl fatty amines wherein the N,N-dialkyl fatty amines forms a lipophilic solvent soluble complex with the glyphosate which is capable of coupling or assisting coupling of the plant nutrients with the lipophilic solvents;
   wherein all proportions are calculated weight/weight on a dry basis based on the total composition.

25. A homogeneous liquid agrochemical composition having a phase stability of at least 48 hours comprising (a) from 2 to 12% of glyphosate;
(b) from 10 to 50% of one or more alkyl esters of fatty acids;
(c) from 2 to 20% of one or more ammonium salts of inorganic anions selected from the group consisting of ammonium sulfate, ammonium phosphate and mixtures thereof; and
(d) from 2 to 20% of one or more N,N-dialkyl fatty amines selected from the group consisting of N,N-dimethyllaurylamine, dimethylcocoamine, oleylamine and mixtures thereof wherein the N,N-dialkyl fatty amines form a lipophilic solvent soluble complex with glyphosate which is capable of coupling or assisting coupling of the plant nutrients with the lipophilic solvents;

wherein all proportions are calculated weight/weight on a dry basis based on the total composition.

26. A homogeneous liquid agrochemical composition having a phase stability of at least 48 hours comprising
(a) from 2 to 12% of glyphosate;
(b) from 10 to 50% of one or more alkyl esters of fatty acids;
(c) from 2 to 20% of one or more ammonium salts of inorganic anions selected from the group consisting of ammonium sulfate, ammonium phosphate and mixtures thereof;
(d) from 2 to 20% of one or more N,N-dialkyl fatty amines selected from the group consisting of N,N-dimethyllaurylamine, dimethylcocoamine, oleylamine and mixtures thereof wherein the N,N-dialkyl fatty amines form a lipophilic solvent soluble complex with glyphosate which is capable of coupling or assisting coupling of the plant nutrients with the lipophilic solvents; and
(e) from 10 to 30% of one or more other components to improve the form a microemulsion;

wherein all proportions are calculated weight/weight on a dry basis based on the total composition.

27. A homogeneous liquid agrochemical composition having a phase stability of at least 48 hours comprising (a) from 2 to 12% of glyphosate;
(b) from 10 to 50% of one or more alkyl esters of fatty acids;
(c) from 2 to 20% of one or more ammonium salts of inorganic anions selected from the group consisting of ammonium sulfate, ammonium phosphate and mixtures thereof;
(d) from 2 to 20% of one or more N,N-dialkyl fatty amines selected from the group consisting of N,N-dimethyllaurylamine, dimethylcocoamine, oleylamine and mixtures thereof wherein the N,N-dialkyl fatty amines form a lipophilic solvent soluble complex with glyphosate which is capable of coupling or assisting coupling of the plant nutrients with the lipophilic solvents; and
(e) from 10 to 30% of one or more other components to form a microemulsion selected from the group consisting of alkyl polysaccharides, fatty alkanolamides, glycols, glycol ethers and mixtures thereof;

wherein all proportions are calculated weight/weight on a dry basis based on the total composition.

28. A method of treating vegetation comprising the step of applying a homogeneous liquid agrochemical composition having a phase stability of at least 48 hours comprising:
(a) glyphosate present in an amount which is not in excess of about 25%;
(b) one or more lipophilic solvents present in an amount which is not in excess of about 80%;
(c) one or more plant nutrients not in excess of about 50%; and
(d) one or more oil soluble bases present in an amount which is not in excess of about 50% wherein the oil soluble base forms a lipophilic solvent soluble complex with glyphosate which is capable of coupling or assisting coupling of the plant nutrients with the lipophilic solvents;

wherein all proportions are calculated weight/weight on a dry basis based on the total composition.

* * * * *